(12) United States Patent
Golz-Berner et al.

(10) Patent No.: US 8,034,385 B2
(45) Date of Patent: Oct. 11, 2011

(54) ANTI-AGEING SKIN COSMETIC

(75) Inventors: Karin Golz-Berner, Monaco (MC); Leonhard Zastrow, Monaco (MC)

(73) Assignee: Coty B.V., Haarlem (NL)

( * ) Notice: Subject to any disclaimer, the term of this patent is extended or adjusted under 35 U.S.C. 154(b) by 1461 days.

(21) Appl. No.: 10/520,562

(22) PCT Filed: Jun. 23, 2003

(86) PCT No.: PCT/DE03/02157
§ 371 (c)(1),
(2), (4) Date: Jan. 7, 2005

(87) PCT Pub. No.: WO2004/004673
PCT Pub. Date: Jan. 15, 2004

(65) Prior Publication Data
US 2006/0002884 A1    Jan. 5, 2006

(30) Foreign Application Priority Data

Jul. 8, 2002 (DE) .................................. 102 31 468

(51) Int. Cl.
| A01N 65/00 | (2009.01) |
| A61K 36/00 | (2006.01) |
| A01N 63/02 | (2009.01) |
| A61K 35/00 | (2006.01) |
| A61M 36/14 | (2006.01) |
| A61K 38/46 | (2006.01) |
| A61K 8/02 | (2006.01) |
| A61K 9/127 | (2006.01) |

(52) U.S. Cl. ...... 424/725; 424/1.21; 424/94.6; 424/401; 424/450; 424/774; 424/777; 424/779; 424/780

(58) Field of Classification Search .................. 424/725, 424/774, 777, 779, 780, 94.6
See application file for complete search history.

(56) References Cited

U.S. PATENT DOCUMENTS

| 5,616,323 A | 4/1997 | Ginoux |
| 6,221,372 B1 | 4/2001 | Golz-Berner |
| 6,426,080 B1 | 7/2002 | Golz-Berner |
| 6,652,868 B1 * | 11/2003 | Simon et al. .................. 424/401 |
| 2002/0048594 A1 | 4/2002 | Breton |
| 2003/0223982 A1 | 12/2003 | Schlotmann |

FOREIGN PATENT DOCUMENTS

| CA | 2335149 | * | 12/2000 |
| DE | 695 21 158 T2 | | 3/2002 |
| DE | 100 63 433 A1 | | 6/2002 |
| EP | 0707844 A2 | * | 4/1996 |
| EP | 1 153 600 A2 | | 11/2001 |
| JP | 61289010 | | 12/1986 |
| JP | 61289010 A | * | 12/1986 |
| JP | 03-206014 | | 9/1991 |
| JP | 07-196526 | | 1/1995 |
| JP | 09-110710 | | 4/1997 |
| JP | 11060496 | * | 3/1999 |
| JP | 11263718 | * | 9/1999 |
| JP | 2000226321 | | 8/2000 |
| JP | 2001 131053 | | 5/2001 |
| JP | 2001226218 | | 8/2001 |
| WO | WO 98/26755 | | 6/1998 |
| WO | WO 99/66881 A2 | | 12/1999 |
| WO | WO 00/35406 | | 6/2000 |
| WO | WO 00/41674 | | 7/2000 |
| WO | WO 00/64472 | * | 11/2000 |
| WO | WO 00/64472 A1 | | 11/2000 |
| WO | WO 01/17495 A1 | | 3/2001 |

* cited by examiner

Primary Examiner — Johann Richter
Assistant Examiner — Mei-Ping Chui
(74) Attorney, Agent, or Firm — Novak Druce + Quigg LLP

(57) ABSTRACT

The invention relates to a cosmetic based on various natural raw materials, which can be used to counter ageing processes of the human skin. The inventive cosmetic contains 0.1-5% by weight of an extract from a mixture of fig leaves and fruits, 0.1-3% by weight of an extract from pomegranate fruits, 0.001-0.5% by weight of a ground dry mixture of rosemary stems and leaves, 0.01-3% by weight of liposomes containing an extract from peeled musk melons, 0.1-5% by weight of liposomes containing a plankton extract containing the photolyase enzyme, 0.1-5% by weight of liposomes containing 0.1 to 0.5% by weight, in relation to the liposome weight, of a micrococcus lysate containing the UV-endonuclease enzyme; and up to 100% by weight, other active substances, carrier substances, adjuvants or mixtures thereof.

8 Claims, No Drawings

8,034,385 B2

ANTI-AGEING SKIN COSMETIC

CROSS REFERENCE TO RELATED APPLICATION

This application is a national stage of PCT/DE2003/002157 filed 23 Jun. 2003 and based upon DE 102 31 468.3 filed 8 Jul. 2002 under the International Convention.

BACKGROUND OF THE INVENTION

1. Field of the Invention

The present invention relates to a cosmetic based on various natural raw materials, which can be used to counter ageing processes of the human skin.

2. Related Art of the Invention

From the state of the art, numerous cosmetics are known which in some way contain plant-based raw materials in the form of oils or extracts. In most cases, the known advantageous effects of individual plants are used to achieve a corresponding overall effect. The effect of rosemary, provided as an oil or an extract from the leaves and sometimes combined with other plant extracts, is e.g. used quite frequently to include antispasmodic and circulation-stimulating properties. Maritime cosmetics often contain algae extracts. For example, WO98/26755 describes a preparation which contains extracts from the *Laminaria saccharina* alga, root extracts from *Lilium candidum* and extracts from *Glycyrrhyza glabra* and achieves a particular skin-cleansing effect. Rosemary extract is used in WO 00/41674 to counter skin ageing.

The object of the invention is to provide an improved cosmetic with a view to skin ageing.

Another object is to develop a cosmetic which at the same time has an improved moisturizing effect.

SUMMARY OF THE INVENTION

According to the invention, an anti-ageing skin cosmetic is therefore provided containing
  0.1 to 5% by weight of an extract from a mixture of fig leaves and fruits;
  0.1 to 3% by weight of an extract from pomegranate fruits;
  0.001 to 0.5% by weight of a ground dry mixture of rosemary stems and leaves;
  0.01 to 3% by weight of liposomes containing an extract from peeled musk melons;
  0.1 to 5% by weight of liposomes containing a plankton extract containing the photolyase enzyme;
  0.1 to 5% by weight of liposomes containing 0.1 to 0.5% by weight, in relation to the liposome weight, of a micrococcus lysate containing the UV-endonuclease enzyme; and
  up to 100% by weight, other active substances, carrier substances, adjuvants or mixtures thereof,
all percentages being relative to the cosmetic's total weight.

DETAILED DESCRIPTION OF THE INVENTION

The fig extract used is an extract consisting of a mixture of leaves and fruits of the *Ficus carica* fig, wherein the two constituents can be contained in a ratio of 25-75:75-25. Said extract is a cold extract (extraction temperature 10-30° C.) obtained with the aid of a water/propylene glycol extractant. The extract contains effective amounts of the proteolytic ficin enzyme and contributes to cell regeneration.

The pomegranate extract obtained from *Punica granatum* is an extract based on water and propylene glycol and stimulates microcirculation in the skin.

Rosemary (*Rosmarinus officinalis*) is not used in the known form of an extract or oil, but as a ground dry mixture of stems and leaves. Such a mixture surprisingly has a high free-radical-scavenging activity and therefore a very high radical protection factor (RPF).

The extract from the musk melon *Cucumis melo*, which is obtained from melons whose outer peel has been removed, using water at a temperature of 10-30° C., helps to reduce the transepidermal water loss (TEWL) and is advantageously incorporated in the cosmetic via liposomes whose outer shell consists of phospholipids and olive oil. This special liposome form noticeably improves the cosmetic's texture.

The plankton extract incorporated via liposomes is e.g. obtained from cyanobacteria of the *Anacystes nidulans* genus and contains an effective amount of the photolyase enzyme. In the presence of daylight, this enzyme contributes to the decomposition of cyclobutane pyrimidine dimers which have been produced due to UV radiation, thus achieving a repair effect for the skin.

It is particularly advantageous that the plankton extract be encapsulated in special liposomes made up of three types of phospholipids: phosphatidylethanolamine, phosphatidylcholine/oleic acid and cholesteryl hemisuccinate. Such liposomes have a great penetration force in keratinocytes and release their contents suddenly when the pH value is reduced, e.g. from pH 6 to pH 4. A preferred product containing said plankton extract is Photosomes® from Barnet Products Corp., NJ/USA.

A micrococcus lysate containing the UV-endonuclease enzyme, which has long-lasting skin repair effects, is also incorporated via liposomes. These liposomes can be embodied in the same advantageous manner described for the plankton extract. A preferred product is Ultrasomes® from Barnet Products Corp., NJ/USA.

The anti-ageing skin effect to be expected from the inventive anti-ageing skin cosmetic due to some of its constituents is by far exceeded by an overall synergetic effect. In addition, the cosmetic achieves an excellent moisture replenishment in the skin which could not be expected from the basic constituents alone.

The inventive cosmetic further contains cosmetic adjuvants and carrier substances as they are commonly used in such preparations, e.g. water, preservatives, colourants, pigments having a colouring effect, thickeners, fragrances, alcohols, polyols, electrolytes, gel-forming agents, oils, polymers, co-polymers, emulsifiers, waxes, stabilizers.

Suitable gel-forming agents include carbomer, xanthan gum, carrageenan, acacia gum, guar gum, agar-agar, alginates and tyloses, carboxymethyl cellulose, hydroxyethyl cellulose, quaternised cellulose, quaternised guar, certain polyacrylates, polyvinyl alcohol, polyvinylpyrrolidone, montmorillonite. Carbomer and hydroxyethyl cellulose are preferred.

The waxes can be selected from among natural plant-based waxes, animal waxes, natural and synthetic mineral waxes and synthetic waxes. These include e.g. carnauba wax, candelilla wax, ozokerite, beeswax, montan wax, wool wax, ceresin, microwaxes, hard paraffin, petrolatum, silicone wax, polyethylene glycol waxes or polyethylene glycol ester waxes. Low-viscosity silicone waxes whose viscosities range up to approx. 1,000 Pa·s are preferred.

Moisturizers used can be glycerine, butylene glycol, propylene glycol and mixtures thereof. Glycerine is preferred.

Further, it is advantageous to add suitable water- and/or oil-soluble UVA or UVB filters or both to the inventive compositions. Advantageous oil-soluble UVB filters include derivatives of 4-aminobenzoic acid such as 4-(dimethylamino)benzoic acid (2-ethylhexyl) ester; esters of cinnamic acid such as 4-methoxycinnamic acid (2-ethylhexyl) ester; benzophenone derivatives such as 2-hydroxy-4-methoxybenzophenone; derivatives of 3-benzylidene camphor such as 3-benzylidene camphor.

Preferred oil-soluble UV filters are Benzophenone-3, Butyl Methoxybenzoylmethane, Octyl Methoxycinnamate, Octyl Salicylate, 4-Methylbenzylidene Camphor, Homosalate, and Octyl Di-methyl PABA.

Water-soluble UVB filters are e.g. sulphonic acid derivatives of benzophenone or of 3-benzylidene camphor, or salts such as the Na or K salt of 2-phenylbenzimidazol-5-sulphonic acid.

UVA filters include derivatives of dibenzoylmethane such as 1-phenyl-4-(4'-isopropylphenyl)propane-1,3-dione.

It is preferred that 2-hydroxy-4-methoxybenzo-phenone-5-sulphonic acid (Benzophenone-4) be used as a water- and alcohol-soluble broad spectrum filter in amounts ranging between 0.1 and 0.5% by weight.

The inventive cosmetic can also contain monovalent and/or polyvalent alcohols, such as ethanol, propylene glycol, dipropylene glycol, ethylene glycol, isoprene glycol, butylene glycols, sorbitol and mixtures thereof. Advantageously, the alkanol and/or polyol are/is contained in amounts ranging between 5 and 20% by weight.

The oils used for the invention can be usual cosmetic oils with low viscosities, such as jojoba oil and silicone oils up to approx. 1,000 Pa·s.

The cosmetic can contain colourants or pigments, pigment mixtures or powders having a pigment-like effect. Pigments can include e.g. iron oxides, natural aluminosilicates such as ochre, titanium (di)oxide, mica, kaolin, clays containing manganese such as umber and red bole, calcium carbonate, talc, mica-titanium oxide, mica-titanium oxide-iron oxide, nylon globules, ceramic globules, expanded and non-expanded synthetic polymer powders, powdery natural organic compounds such as ground solid algae, ground plant parts, encapsulated and non-encapsulated cereal starch.

Further active substances contained can be antioxidants and scavengers. Such substances include vitamins such as vitamin C and derivatives thereof, e.g. ascorbyl acetate, ascorbyl phosphate and ascorbyl palmitate; vitamin A and derivatives thereof; folic acid and derivatives thereof; vitamin E and derivatives thereof such as tocopheryl acetate; flavons or flavonoids; amino acids such as histidine, glycine, tyrosine, tryptophan and derivatives thereof; carotenoids and carotenes such as e.g. α-carotene, β-carotene; uric acid and derivatives thereof; α-hydroxy acids such as citric acid, lactic acid, malic acid; stilbenes and derivatives thereof.

A particularly preferred active substance is an active formulation containing (a) a product obtained by extracting the bark of *Quebracho blanco* and subsequent enzymatic hydrolysis, which product contains at least 90% by weight proanthocyanidine oligomers and max. 10% by weight gallic acid, (a), whose active substance concentration is 2% by weight, bound to microcapsules, being contained in an amount ranging between 0.1 and 10% by weight; (b) a silkworm extract obtained by extraction, which extract contains the cecropine peptide, amino acids and a vitamin mixture, (b) being contained in an amount ranging between 0.1 and 10% by weight; (c) a non-ionic, cationic or anionic hydro-gel or hydrogel mixture, (c) being contained in an amount ranging between 0.1 and 5% by weight; wherein the active substances (a) and (b) form an association complex together with the gel (c) and one or several phospholipid(s) contained in an amount between 0.1 and 30% by weight and with water, and each of the aforesaid percentages is in relation to the total weight of the active formulation.

In a preferred embodiment, the anti-ageing skin cosmetic consists of
  0.1 to 1% by weight of an extract from fig leaves and fruits;
  0.1 to 1% by weight of an extract from pomegranate fruits;
  0.001 to 0.1% by weight of a ground dry mixture of rosemary stems and leaves;
  0.01 to 1% by weight of an extract from peeled musk melons;
  0.1 to 1% by weight of liposomes containing a plankton extract containing the photolyase enzyme;
  0.1 to 1% by weight of liposomes containing 0.1 to 0.5% by weight, in relation to the liposome weight, of a micrococcus lysate containing the UV-endonuclease enzyme;
  60 to 80% by weight water;
  0.1 to 1% by weight of a silicone wax;
  0.3 to 0.7% by weight of a preservative or preservative mixture;
  0.01 to 0.5% by weight Na-EDTA (Tetrasodium Ethylenediamine Tetraacetic Acid);
  1 to 10% by weight Butane Diol 1.3/1,3 Butylene Glycol U-Pur;
  0.1 to 0.5% by weight Carbomer;
  0.1 to 0.5% by weight Hydroxyethyl Cellulose;
  0.1 to 0.5% by weight Triethanolamine;
  0.1 to 1% by weight Xanthan Gum;
  1 to 5% by weight Glycerine;
  1 to 15% by weight Ethanol;
  0.1 to 0.5% by weight of an active formulation containing (a) a product obtained by extracting the bark of *Quebracho blanco* and subsequent enzymatic hydrolysis, which product contains at least 90% by weight proanthocyanidine oligomers and max. 10% by weight gallic acid, (a), whose active substance concentration is 2% by weight, bound to micro-capsules, being contained in an amount ranging between 0.1 and 10% by weight; (b) a silkworm extract obtained by extraction, which extract contains the cecropine peptide, amino acids and a vitamin mixture, (b) being contained in an amount ranging between 0.1 and 10% by weight; (c) a non-ionic, cationic or anionic hydro-gel or hydrogel mixture, (c) being contained in an amount ranging between 0.1 and 5% by weight; wherein the active substances (a) and (b) form an association complex together with the gel (c) and one or several phospholipid(s) contained in an amount between 0.1 and 30% by weight and with water, and each of the aforesaid percentages is in relation to the total weight of the active formulation;
  0.2 to 0.5% by weight PEG 40;
  0.1 to 0.5% by weight Benzophenone-4; and optionally 0.1 to 1% by weight of colourant and perfume respectively,
all percentages being relative to the total weight of the cosmetic complex unless indicated otherwise.

Overall, the preferred embodiment has a very good anti-ageing effect, which could be proved by means of comparative tests. It also has an excellent moisturizing effect according to corneometer measurements carried out.

The radical protection factor of the inventive cosmetic ranges between 40 and $100 \times 10^{14}$ radicals/mg. The radical protection factor (RPF) defines the free-radical-scavenging activity by means of an antioxidant compared to a test substance. The measurement was carried out as described in WO 99/66881.

The invention will now be explained in more detail by means of examples. All quantities are in percent by weight unless indicated otherwise.

Example 1

Facial Serum I

| | |
|---|---|
| Water | q.s. ad 100 |
| Silicone wax | 0.5 |
| Preservative | 0.5 |
| Tetrasodium EDTA | 0.1 |
| Butane Diol 1.3/Butylene Glycol U-Pur | 5.0 |
| Carbomer | 0.2 |
| Hydroxyethyl Cellulose | 0.2 |
| Triethanolamine | 0.2 |
| Xanthan Gum | 0.6 |
| Glycerine | 1.5 |
| Ethanol | 10.0 |
| Fig extract | 0.5 |
| Pomegranate extract | 0.5 |
| Active formulation* | 0.1 |
| Rosemary powder | 0.001 |
| Melon liposomes | 0.1 |
| Perfume | 0.1 |
| PEG 40 | 0.3 |
| Colourant | q.s. |
| Plankton liposomes (Photosomes) | 0.1 |
| Lysate liposomes (Ultrasomes) | 0.1 |
| Benzophenone-4 | 0.1 |

*containing Quebracho blanco (2%), silkworm extract (1%), dry gel (1%), phospholipids (7%) and water (89%); prepared as described in WO99/66881, Example 1.

The serum was prepared at 45° C. Wax was added into the heated water and stirred. Carbomer was then added, stirred thoroughly and neutralized. Subsequently, the remaining raw materials were added at room temperature while stirring. Finally, the mixture was homogenized. The serum's RPF was 67.

Example 2

Facial Serum II

| | |
|---|---|
| Water | q.s. ad 100 |
| Silicone wax | 0.9 |
| Preservative | 0.3 |
| Tetrasodium EDTA | 0.2 |
| Butane Diol 1.3/Butylene Glycol U-Pur | 7.0 |
| Carbomer | 0.3 |
| Hydroxyethyl Cellulose | 0.1 |
| Triethanolamine | 0.3 |
| Xanthan Gum | 0.5 |
| Glycerine | 1.0 |
| Ethanol | 5.0 |
| Fig extract | 1.0 |
| Pomegranate extract | 1.5 |
| Active formulation* | 0.5 |
| Rosemary powder | 0.01 |
| Melon liposomes | 2.0 |
| Perfume | 0.01 |
| PEG 40 | 0.1 |
| Colourant | q.s. |
| Plankton liposomes (Photosomes) | 0.5 |
| Lysate liposomes (Ultrasomes) | 0.5 |
| Benzophenone-4 | 0.2 |
| Silicone | 2.0 |

*containing Quebracho blanco (2%), silkworm extract (1%), dry gel (1%), phospholipids (7%) and water (89%); prepared as described in WO99/66881, Example 1.
The lotion was prepared as in Example 1. The serum's RPF was 69.

Example 3

Test Example (A) Anti-Ageing Effect

Consumer tests were carried out with 150 consumers who applied the serum according to Example 1 to their face for four weeks and completed a questionnaire.

Of those surveyed who had used the product regularly in the mornings and evenings (82%), 39% judged that a "noticeable result was achieved", 32% that a "partly noticeable result was achieved" and 11% that "no noticeable result was achieved".

Specifically, the following results were achieved:

| | | |
|---|---|---|
| Increase in skin elasticity | after 1 week | in 77%* |
| | after 2 weeks | in 87% |
| | after 3 weeks | in 84% |
| Reduction of fine lines | after 1 week | in 76%* |
| | after 2 weeks | in 81% |
| | after 3 weeks | in 83% |
| Appearance of the skin (firmness) | after 1 week | in 81%* |
| | after 2 weeks | in 84% |
| | after 3 weeks | in 84% |

*of the test persons

It was particularly surprising that 96% of the test persons were able to note an immediate effect after 1-2 days and that the effect was clearly noticeable in a high percentage of the participants after 1 week.

A comparative test with 20 test persons who applied the serum according to Example 1 in the same manner, except that the serum did not contain rosemary powder and pomegranate extract, showed a delayed improvement effect and lower values:

| | | |
|---|---|---|
| Increase in skin elasticity | after 1 week | in 52%* |
| | after 2 weeks | in 58% |
| | after 3 weeks | in 51% |
| Reduction of fine lines | after 1 week | in 33%* |
| | after 2 weeks | in 43% |
| | after 3 weeks | in 45% |
| Appearance of the skin (firmness) | after 1 week | in 45%* |
| | after 2 weeks | in 53% |
| | after 3 weeks | in 58% |

*of the test persons

These pronounced differences suggest a synergy.

(B) Moisturizing Effect

In the context of the consumer test according to (A), the consumers assessed the moisturizing effect and graded it as follows:
  little moisturizing effect
  normal moisturizing effect
  long-lasting moisturizing effect (>24 hours).
18% of all consumers judged that there was a "normal moisturizing effect" and 79% that there was a "long-term moisturizing effect". 3% made no statement.

These results prove an excellent moisturizing effect and a very good anti-ageing effect.

We claim:
1. An anti-ageing skin cosmetic comprising:
   0.1 to 5% by weight of an extract from a mixture of fig leaves and fruits;
   0.1 to 3% by weight of an extract from pomegranate fruits;

0.001 to 0.5% by weight of a ground dry mixture of rosemary stems and leaves;
0.01 to 3% by weight of liposomes containing an extract from peeled musk melons;
0.1 to 5% by weight of liposomes containing a plankton extract containing a photolyase enzyme;
0.1 to 5% by weight of liposomes containing 0.1 to 0.5% by weight, in relation to the liposome weight, of a micrococcus lysate containing a UV-endonuclease enzyme; and
up to 100% by weight, other active substances, carrier substances, adjuvants or mixtures thereof, all percentages being relative to the cosmetic's total weight.

2. The anti-ageing skin cosmetic according to claim 1, wherein the liposomes containing the musk melon extract are made up of phospholipids and olive oil.

3. The anti-ageing skin cosmetic according to claim 1, wherein the plankton extract stems from the *Anacystes nidulans* cyanobacterium.

4. The anti-ageing skin cosmetic according to claim 1, wherein the liposomes containing the plankton extract consist of a mixture of phosphatidyl ethanol-amine, phosphatidyl-choline, oleic acid and cholesteryl hemisuccinate.

5. An anti-ageing skin cosmetic, wherein said cosmetic comprises
0.1 to 1% by weight of an extract from fig leaves and fruits;
0.1 to 1% by weight of an extract from pomegranate fruits;
0.001 to 0.1% by weight of a ground dry mixture of rosemary stems and leaves;
0.01 to 1% by weight of an extract from peeled musk melons;
0.1 to 1% by weight of liposomes containing a plankton extract containing a photolyase enzyme;
0.1 to 1% by weight of liposomes containing 0.1 to 0.5% by weight, in relation to the liposome weight, of a micrococcus lysate containing a UV-endonuclease enzyme;
60 to 80% by weight water;
0.1 to 1% by weight of a silicone wax;
0.3 to 0.7% by weight of a preservative or preservative mixture;
0.01 to 0.5% by weight Na-EDTA (Tetrasodium Ethylenediamine Tetraacetic Acid);
1 to 10% by weight Butane Diol 1.3/1,3 Butylene Glycol U-Pur;
0.1 to 0.5% by weight Carbomer;
0.1 to 0.5% by weight Hydroxyethyl Cellulose;
0.1 to 0.5% by weight Triethanolamine;
0.1 to 1% by weight Xanthan Gum;
1 to 5% by weight Glycerine;
1 to 15% by weight Ethanol;
0.1 to 0.5% by weight of an active formulation containing
(a) a product obtained by extracting a bark of *Quebracho blanco* and subsequent enzymatic hydrolysis, which product contains at least 90% by weight proanthocyanidine oligomers and max. 10% by weight gallic acid,
(a), whose active substance concentration is 2% by weight, bound to micro-capsules, being contained in an amount ranging between 0.1 and 10% by weight;
(b) a silkworm extract obtained by extraction, which extract contains a cecropine peptide, amino acids and a vitamin mixture, (b) being contained in an amount ranging between 0.1 and 10% by weight;
(c) a non-ionic, cationic or anionic hydro-gel or hydro-gel mixture, (c) being contained in an amount ranging between 0.1 and 5% by weight; wherein the active substances (a) and (b) form an association complex together with the gel (c) and one or several phospholipid(s) contained in an amount between 0.1 and 30% by weight and with water, and each of the aforesaid percentages is in relation to the total weight of the active formulation;
0.2 to 0.5% by weight PEG 40;
0.1 to 0.5% by weight Benzophenone-4;
optionally 0.1 to 1% by weight of colourant and perfume respectively, all percentages being relative to the total weight of the cosmetic complex unless indicated otherwise; and up to 100% by weight, other active substances, carrier substances, adjuvants or mixtures thereof, all percentages being relative to the cosmetic's total weight.

6. A method for reducing wrinkles and for prolonging the period for a visibly wrinkle-free skin, said method comprising applying to skin an anti-ageing skin cosmetic comprising:
0.1 to 5% by weight of an extract from a mixture of fig leaves and fruits;
0.1 to 3% by weight of an extract from pomegranate fruits;
0.001 to 0.5% by weight of a ground dry mixture of rosemary stems and leaves;
0.01 to 3% by weight of liposomes containing an extract from peeled musk melons;
0.1 to 5% by weight of liposomes containing a plankton extract containing a photolyase enzyme;
0.1 to 5% by weight of liposomes containing 0.1 to 0.5% by weight, in relation to the liposome weight, of a micrococcus lysate containing a UV-endonuclease enzyme; and
up to 100% by weight, other active substances, carrier substances, adjuvants or mixtures thereof, all percentages being relative to the cosmetic's total weight.

7. The anti-ageing skin cosmetic according to claim 1, wherein the extract from a mixture of fig leaves and fruits further comprises a proteolytic ficin enzyme and wherein the extract from a mixture of fig leaves and fruits has a weight ratio of leaves-to-fruit ranging from 25:75 to 75:25.

8. The method according to claim 6, wherein the extract from a mixture of fig leaves and fruits further comprises a proteolytic ficin enzyme and wherein the extract from a mixture of fig leaves and fruits has a weight ratio of leaves-to-fruit ranging from 25:75 to 75:25.

* * * * *